United States Patent [19]

Walker et al.

[11] Patent Number: 5,593,867
[45] Date of Patent: Jan. 14, 1997

[54] FLUORERSCENCE POLARIZATION DETECTION OF NUCLEIC ACID AMPLICATION

[75] Inventors: G. Terrance Walker; James G. Nadeau, both of Chapel Hill; C. Preston Linn, Durham, all of N.C.

[73] Assignee: Becton, Dickinson and Company, Franklin Lakes, N.J.

[21] Appl. No.: 311,474

[22] Filed: Sep. 23, 1994

Related U.S. Application Data

[63] Continuation-in-part of Ser. No. 229,281, Apr. 18, 1994.
[51] Int. Cl.$^6$ ............................ C12P 19/34; C12Q 1/68
[52] U.S. Cl. ............................ 435/91.2; 435/6; 935/78
[58] Field of Search ........................ 435/6, 91.2, 91, 435/94; 935/78

[56] References Cited

U.S. PATENT DOCUMENTS 5,270,184  12/1993  Walker et al. ........................ 435/91.2

FOREIGN PATENT DOCUMENTS

| 0382433 | 8/1990 | European Pat. Off. . | |
| 0382433A2 | 8/1990 | European Pat. Off. | C12Q 1/68 |
| 0500224 | 8/1992 | European Pat. Off. . | |
| 0512334 | 11/1992 | European Pat. Off. . | |
| WO90/06374 | 6/1990 | WIPO . | |
| WO92/18650 | 10/1992 | WIPO . | |
| WO93/10267 | 5/1993 | WIPO . | |
| WO93/09250 | 5/1993 | WIPO . | |
| WO93/16194 | 8/1993 | WIPO . | |
| WO94/12665 | 6/1994 | WIPO | C12Q 1/68 |

OTHER PUBLICATIONS

Cook, J. et al. Detection of Protein–DNA Complex Formation by Time–Resolved Fluorescence Polarization . . . Anal. Biochem. (1990) 190:331–339.
Wright, D. et al. The Negative Charge of Glu–III is Required to Activate the Cleavage Center of EcoRi Endonuclease (1989) 264:11816–11821.

G. T. Walker, et al. "Isothermal in vitro amplification of DNA by a restriction enzyme/DNA polymerase system", *Proc. Natl. Acad. Sci. USA* 89, 392–396 (1992).
G. T. Walker, et al. "Strand displacement amplification—an isothermal, in vitro DNA amplification technique" *Nucl. Acids Res.* 20, 1691–1696 (1992).
R. Devlin, et al. "Homogeneous detection of nucleic acids by transient–state polarized fluorescence" *Clin. Chem.* 39, 1939–1943 (1993).
G. T. Walker, et al. "Multiplex strand displacement amplification (SDA) and detection of DNA sequences from Mycobacterium tuberculosis and other mycobacteria" *Nucl. Acids Res.* 22, 2670–2677 (1994).
C. A. Spargo, et al. "Chemiluminescent detection of strand displacement amplified DNA from species comprising the Mycobacterium tuberculosis complex" *Molec. Cell. Probes* 7, 395–404 (1993).
A. Murakami, et al. "Fluorescent–labeled oligonucleotide probes: detection of hybrid formation in solution by fluorescence polarization spectroscopy" *Nucl. Acids Res.* 19, 4097–4102 (1991).
J. C. Guatelli, et al. "Isothermal, in vitro amplification of nucleic acids by a multienzyme reaction modeled after retroviral replication" *Proc. Natl. Acad. Sci. USA* 87, 1874–1878 (1990).

*Primary Examiner*—Stephanie W. Zitomer
*Assistant Examiner*—Amy Atzel
*Attorney, Agent, or Firm*—Donna R. Fugit

[57] ABSTRACT

Fluorescence polarization methods for detection of nucleic acid amplification. A fluorescently labelled oligodeoxynucleotide probe is converted from single- to double-stranded form in a target dependent manner during amplification of the target sequence. This conformational change is accompanied by an increase in fluorescence polarization values. The increase in fluorescence polarization can be measured on a transient-state fluorometer in real-time during the amplification reaction without any physical manipulation of the sample. The inventive methods therefore provide a closed, homogeneous system for both amplification of target sequences and detection of amplification. Alternatively, amplification may be detected in the fluorometer after the amplification reaction is completed.

18 Claims, 11 Drawing Sheets

FIG-8

Legend: No EcoRI (Gln111); EcoRI (Gln111)

Y-axis: FLUORESCENCE POLARIZATION (mP), 0 to 120

X-axis: INITIAL M. tb TARGETS: $10^5$, $10^4$, $10^3$, $10^2$, 10, 0, $10^5$ NO SDA

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCATTATAGT ACCTGTCTGT TGACACTGAG ATCCCCT                                    3 7

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTGAATAGTC GGTTACTTGT TGACGGCGTA CTCGACC                                    3 7

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGGACCCGCC AAC                                                              1 3

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGCTGAACCG GAT 13

( 2 ) INFORMATION FOR SEQ ID NO:5:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

TGAAAGACGT TATCCACCAT ACGGATAG 28

( 2 ) INFORMATION FOR SEQ ID NO:6:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GGAATTCATC CGTATGGTGG ATAACGTCTT TCA 33

( 2 ) INFORMATION FOR SEQ ID NO:7:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

ATCCGTATGG TGGATAACGT CTTTCA 26

( 2 ) INFORMATION FOR SEQ ID NO:8:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

TGAAAGACGA CGTTATCCAC CATACGGATG AATTCC 36

( 2 ) INFORMATION FOR SEQ ID NO:9:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

TGAAAGACGT TATCCACCAT ACGGAT 26

FLUORERSCENCE POLARIZATION DETECTION OF NUCLEIC ACID AMPLICATION

This application is a continuation-in-part of U.S. Ser. No. 08/229,281, filed Apr. 18, 1994.

FIELD OF THE INVENTION

The present invention relates to methods for detecting amplification of nucleic acid target sequences and in particular to detection of amplification by fluorescence polarization.

BACKGROUND OF THE INVENTION

Strand Displacement Amplification (SDA) utilizes the ability of a restriction enzyme to nick a hemimodified recognition site and the ability of a polymerase to displace a downstream DNA strand to amplify a target nucleic acid (U.S. Pat. No. 5,270,184, hereby incorporated by reference; Walker, et al. 1992. *Proc. Natl. Acad. Sci. USA* 89, 392–396; Walker, et al. 1992. *Nucl. Acids Res.* 20, 1691–1696). The target for SDA may be present on fragments of nucleic acid generated by treatment with a restriction endonuclease, or targets appropriate for SDA may be generated by extension and displacement of primers. This second type of target generation and the subsequent steps of the SDA reaction are illustrated in FIG. 1. The target generation process (left side of FIG. 1) produces copies of the target sequence flanked by the nickable restriction sites required for SDA. These modified target sequences are exponentially amplified by repeated nicking, strand displacement, and repriming of displaced strands (right side of FIG. 1). Despite the apparent complexity of FIG. 1, SDA operates under a very simple protocol: double-stranded target DNA is heat denatured in the presence of all reagents except the restriction enzyme and polymerase. Exponential amplification then proceeds at a constant, reduced temperature upon addition of the enzymes, without any further manipulation of the reaction. SDA is capable of $10^8$-fold amplification of target sequences in 2 hours at a constant reaction temperature, usually about 35°–42° C.

Fluoresence Polarization (FP) is a measure of the time-average rotational motion of fluorescent molecules. It has been known since the 1920's and has been used in both research and clinical applications for sensitive determination of molecular volume and microviscosity. The FP technique relies upon changes in the rotational properties of molecules in solution. That is, molecules in solution tend to "tumble" about their various axes. Larger molecules (e.g., those with greater volume or molecular weight) tumble more slowly and along fewer axes than smaller molecules. They therefore move less between excitation and emission, causing the emitted light to exhibit a relatively higher degree of polarization. Conversely, fluorescence emissions from smaller fluorescent molecules, which exhibit more tumbling between excitation and emission, are more multiplanar (less polarized). When a smaller fluorescent molecule takes a larger or more rigid conformation its tumbling decreases and the emitted fluorescence becomes relatively more polarized. This change in the degree of polarization of emitted fluorescence can be measured and used as an indicator of increased size and/or rigidity of the fluorescent molecule.

In fluorescence polarization techniques, the fluorescent molecule is first excited by polarized light. The polarization of the emission is measured by measuring the relative intensities of emission (i) parallel to the plane of polarized excitation light and (ii) perpendicular to the plane of polarized excitation light. A change in the rate of tumbling due to a change in size and/or rigidity is accompanied by a change in the relationship between the plane of excitation light and the plane of emitted fluorescence, i.e., a change in fluorescence polarization. Such changes can occur, for example, when a single stranded oligonucleotide probe becomes double stranded or when a nucleic acid binding protein binds to an oligonucleotide. Fluorescence anisotropy is closely related to FP. This technique also measures changes in the tumbling rates of molecules but is calculated using a different equation. It is to be understood that polarization and anisotropy are interchangeable techniques for use in the present invention. The term fluorescence polarization is generally used herein but should be understood to include fluorescence anisotropy methods. In steady state measurements of polarization and anisotropy, these values are calculated according to the following equations:

$$P \text{ (polarization)} = \frac{Ipa - Ipe}{Ipa + Ipe}$$

$$r \text{ (anisotropy)} = \frac{Ipa - Ipe}{Ipa + 2IPe}$$

where Ipa is the intensity of fluorescence emission parallel to the plane of polarized excitation light and Ipe is the intensity of fluorescence emission perpendicular to the plane of polarized excitation light.

As FP is homogenous, this technique is ideal for studying molecular interactions in solution without interference by physical manipulation. Fluorescence polarization is therefore a convenient method for monitoring conversion of single-stranded fluorescently labelled DNA to double-stranded form by hybridization (Murakami, et al. 1991. *Nucl. Acids Res.* 19, 4097–4102). The ability of FP to differentiate between single and double-stranded nucleic acid conformations without physical separation of the two forms has made this technology an attractive alternative for monitoring probe hybridization in diagnostic formats. European Patent Publication No. 0 382 433 describes fluorescence polarization detection of amplified target sequences by hybridization of a fluorescent probe to the amplicons or by incorporation of a fluorescent label into the amplification products by target-specific extension of a fluorescently-labeled amplification primer. PCT Patent Publication No. WO 92/18650 describes similar methods for detecting amplified RNA or DNA target sequences by the increase in fluorescence polarization associated with hybridization of a fluorescent probe.

Fluorescence polarization may be monitored as either transient state FP or steady state FP. In transient state FP, the excitation light source is flashed on the sample and polarization of the emitted light is monitored by turning on the photomultiplier tube after the excitation light source is turned off. This reduces interference from light scatter, as fluorescence lasts longer than light scatter, but some fluorescence intensity is lost. In steady state FP, excitation light and emission monitoring are continuous (i.e., the excitation source and photomultiplier tube are on continuously). This results in measurement of an average tumbling time over the monitoring period and includes the effects of scattered light.

The present invention provides FP or fluorescence anisotropy detection methods for use with nucleic acid amplification methods such as SDA. Previously, SDA-amplified target sequences were detected following amplification using $^{32}$P-probes (Walker, et al. 1992 *Nucl. Acids Res.*, supra) or by a sandwich hybridization assay with chemiluminescent signal generation (Spargo, et al. 1993. *Molec. Cell. Probes* 7, 395–404). Both of these detection formats require separation of free and bound detector probe before the signal can be measured. However, the ability to differentiate free and bound probe using FP without physical separation enables performance of SDA and detection of amplification in a homogeneous, closed system. Furthermore, it has been discovered that SDA and FP detection can be combined in a single step (i.e., real-time amplification and detection), in part as a result of the isothermal nature of SDA. A closed, homogeneous assay reduces operating steps and procedural complexity, as well as providing improved control of the dispersal of amplification products in the laboratory, thereby reducing the potential for false positives due to accidental contamination of samples with target DNA.

Certain of the terms and phrases used herein are defined as follows:

An amplification primer is a primer for amplification of a target sequence by primer extension or ligation of adjacent primers hybridized to the target sequence. For amplification by SDA, the oligonucleotide primers are preferably selected such that the GC content is low, preferably less than 70% of the total nucleotide composition of the probe. Similarly, for SDA the target sequence preferably has a low GC content to minimize secondary structure. The 3' end of an SDA amplification primer (the target binding sequence) hybridizes at the 3' end of the target sequence. The target binding sequence confers target specificity on the amplification primer. The SDA amplification primer further comprises a recognition site for a restriction endonuclease near its 5' end. The recognition site is for a restriction endonuclease which will nick one strand of a DNA duplex when the recognition site is hemimodified, as described by Walker, et al. (1992. *Proc. Natl. Acad. Sci.* and *Nucl. Acids Res., supra*). The SDA amplification primer generally also comprises additional sequences 5' to the restriction endonuclease recognition site to allow the appropriate restriction endonuclease to bind to its recognition site and to serve as a primer for the polymerase after nicking, as is known in the art. For the majority of the SDA reaction, the amplification primer is responsible for exponential amplification of the target sequence. The SDA amplification primer may also be referred to as the "S" primer, e.g., $S_1$ and $S_2$ when a pair of amplification primers is used for amplification of a double stranded sequence. For other amplification methods which do not require attachment of specialized sequences to the ends of the target, the amplification primer generally consists of only the target binding sequence.

A bumper or external primer is a primer used in SDA which anneals to a target sequence upstream of the amplification primer such that extension of the bumper primer displaces the downstream primer and its extension product. Bumper primers may also be referred to as "B" primers, e.g., $B_1$ and $B_2$ when a pair of bumper primers is used to displace the extension products of a pair of amplification primers. Extension of bumper primers is one method for displacing the extension products of amplification primers, but heating is also suitable.

The terms target or target sequence refer to nucleic acid sequences amplifiable by amplification primers. These include the original nucleic acid sequence to be amplified, the complementary second strand of the original nucleic acid sequence to be amplified, and either strand of a copy of the original sequence which is produced by the amplification reaction. These copies also serve as amplifiable target sequences by virtue of the fact that they also contain copies of the original target sequences to which the amplification primers hybridize.

Copies of the target sequence which are generated during the amplification reaction are referred to as amplification products, amplimers or amplicons.

The term extension product refers to the single-stranded copy of a target sequence produced by hybridization of a primer and extension of the primer by polymerase using the target sequence as a template.

SUMMARY OF THE INVENTION

The present invention provides methods for detection of nucleic acid amplification using FP and a detector probe comprising a fluorescent dye. Amplification is detected as an increase in FP associated with target-dependent formation of double-stranded fluorescent products from the single-stranded detector probe. In one embodiment, the invention also relates to a novel technique that can be used to enhance the magnitude of the increase in FP which results from formation of double-stranded DNA. Enhancing the magnitude of this change is advantageous because there is otherwise only about a 20 mP difference between single-stranded FP values and double-stranded FP values for a fluorescein labelled oligonucleotide. It has been found that double-stranded DNA binding proteins can be used to enhance the increase in FP associated with the single- to double-stranded conversion. In one example, the double-stranded DNA binding protein is the restriction endonuclease EcoRI, which in its natural form requires magnesium to cut the DNA to which it binds. In the absence of magnesium, EcoRI binds but does not cut, and under these conditions can be used to enhance the increase in FP associated with single- to double-stranded conversion. In a second example, the DNA binding protein is a mutant form of EcoRI, designated EcoRI (Gln 111) and described by Wright, et. al. (1989. *J. Biol. Chem.* 264, 11816–11821). EcoRI (Gln 111) binds more tightly than natural EcoRI to double-stranded DNA but does not cut the nucleic acid even in the presence of magnesium. Binding of this protein also enhances the increase in FP which accompanies conversion to double-stranded form.

DESCRIPTION OF THE DRAWINGS

FIG. 8 is a graph illustrating FP values obtained upon amplification of various initial amounts of target sequence with post-amplification addition of EcoRI (Gln 111), using a detector probe which contains an EcoRI recognition site.

DETAILED DESCRIPTION OF THE INVENTION

Figure 1A:
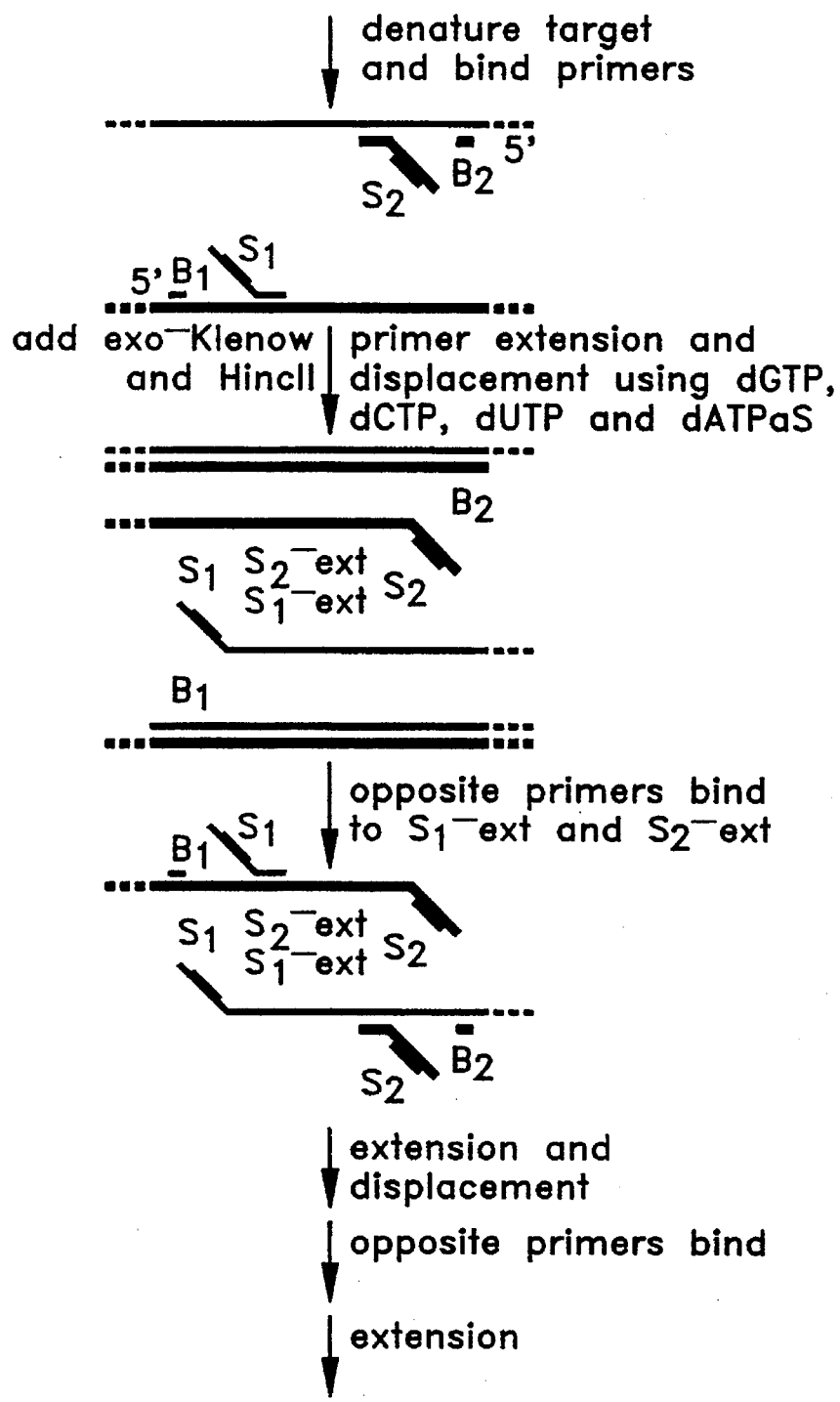
FIG. 1 illustrates the target generation scheme for SDA (left side) and the reaction steps for exponential amplification of a target sequence by SDA (right side).
Figure 1B:
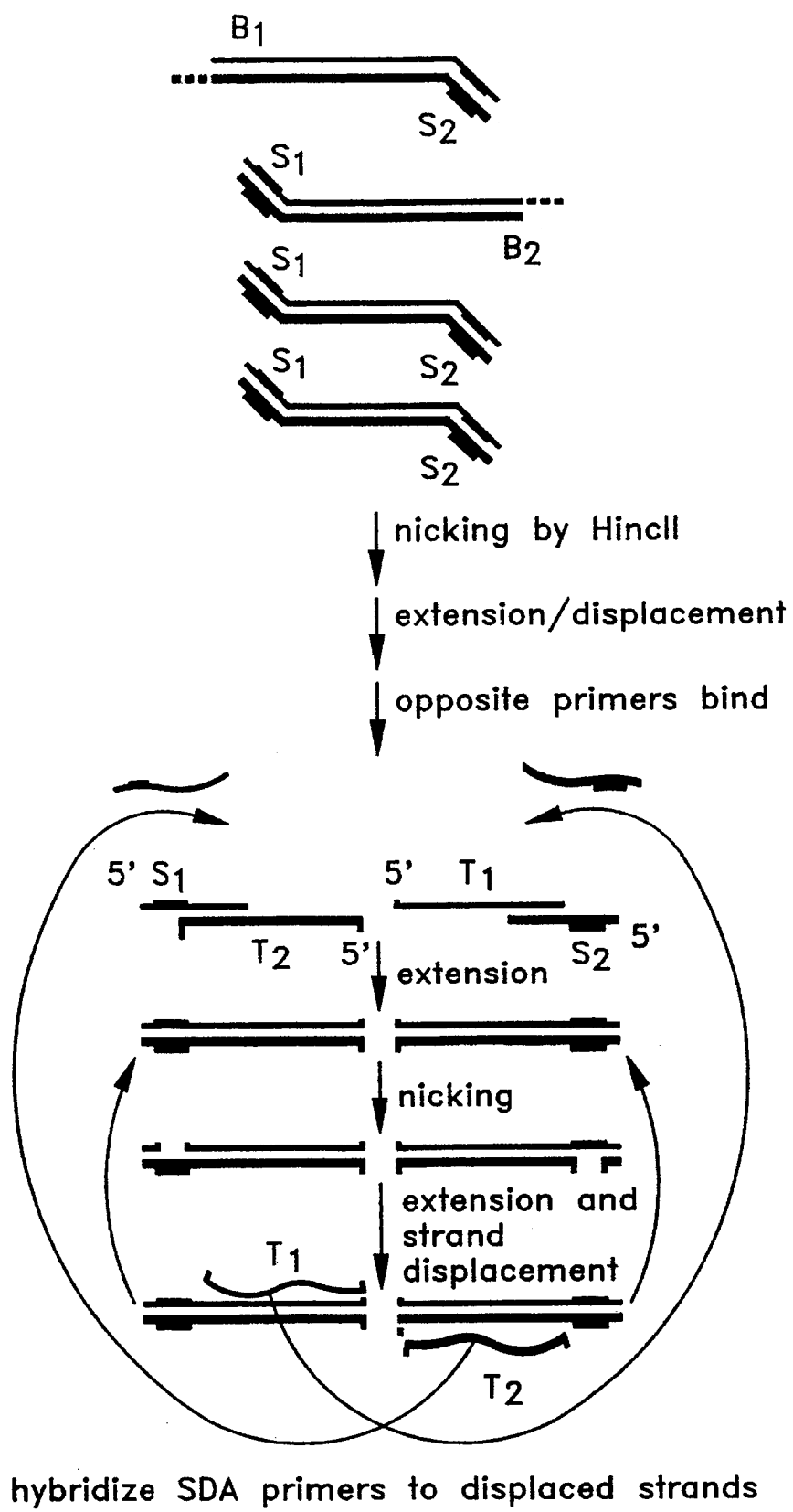

The Strand Displacement Amplification target generation and amplification reaction schemes are illustrated in FIG. 1. The target DNA is heat denatured in the presence of an excess of four primers ($B_1$, $B_2$, $S_1$ and $S_2$). $S_1$ and $S_2$ are amplification primers containing target binding sequences at their 3' ends and a recognition site for a restriction endonuclease (e.g., HincII - $^5$GTTGAC) at a position 5' to the target binding sequences. The restriction endonuclease recognition sites are designated by the raised boxes. For convenience, the following description will use HincII and exo$^-$ Klenow as examples, however, any of the restriction enzymes and exonuclease deficient polymerases known for use in SDA may be substituted.

$S_1$ and $S_2$ hybridize to the opposite, complementary strands of the double stranded target sequence, flanking the region to be amplified. $B_1$ and $B_2$ are external or bumper primers which consist only of target binding sequences and hybridize at positions 5' to $S_1$ and $S_2$. After annealing of the primers to the target at about 40° C., HincII is added along with an exonuclease deficient form of the Klenow fragment of *E. coli* DNA polymerase I (exo$^-$ Klenow). At this point the remaining target generation steps on the left side of FIG. 1 proceed as a single cascade. Exo$^-$ Klenow, which is present in large molar excess over the number of target sequences, simultaneously extends all four primers using dGTP, dCTP, dUTP (or TTP) and dATPαS (deoxyadenosine 5'-[α-thio]triphosphate). $S_1$ and $S_2$ are extended and their extension products are displaced by extension of $B_1$ and $B_2$. The displaced extension products of $S_1$ and $S_2$ ($S_1$-ext and $S_2$-ext) serve as targets for binding of the opposite amplification primers. Further rounds of extension and displacement produce two target fragments with a hemiphosphorothioate HincII site at each end and two longer target fragments with a hemiphosphorothioate HincII site at only one end (bottom left side of FIG. 1). Incorporation of dATPαS in place of dATP in one of the two strands by the polymerase causes the restriction endonuclease to nick one strand rather than cleave both strands of the duplex. "Nicking" refers to cleavage of one strand of double stranded DNA as opposed to double stranded cleavage. HincII nicks the unmodified primer strands of the hemiphosphorothioate recognition sites, leaving intact the modified complementary strands. Exo$^-$ Klenow then extends from the 3'-end of the nick and displaces the downstream newly synthesized strand. New $S_1$ and $S_2$primers bind to the displaced strands and are extended. This is followed by additional nicking and strand displacement steps until the four duplexes at the bottom left side of FIG. 1 converge into the "steady-state" amplification cycle illustrated on the fight side of FIG. 1. During each SDA cycle, the 3' end of $S_1$ hybridizes to the 3'-end of the displaced target strand $T_2$, forming a duplex with 5'-overhangs. Likewise, $S_2$ binds to displaced $T_1$. Exo$^-$ Klenow extends the recessed 3'-ends of the duplexes producing hemiphosphorothioate recognition sites which are nicked by HincII. These nicking and extension/displacement steps cycle continuously (short curved arrows on the right side of FIG. 1) because extension at a nick regenerates a nickable HincII recognition site. The strand displaced from the $S_1$-$T_2$ duplex is identical to $T_1$. Likewise, the displaced strand from the $S_2$-$T_1$ duplex is identical to $T_2$. Consequently, target amplification is exponential because each displaced $T_2$ binds a new $S_1$ primer and each displaced $T_1$ binds a new $S_2$ (long curved arrows on the fight side of FIG. 1). Sense and antisense strands are differentiated by thin and thick lines. Intact and nicked HincII recognition sites are represented by ▃▪▃ and ⌐ ∟. The partial HincII recognition sites (5'-GAC and its complement 5'-GTC) are present at the 5'-and 3'-ends of displaced strands and are represented by ∟ and ⌐, respectively.

Figure 2A:
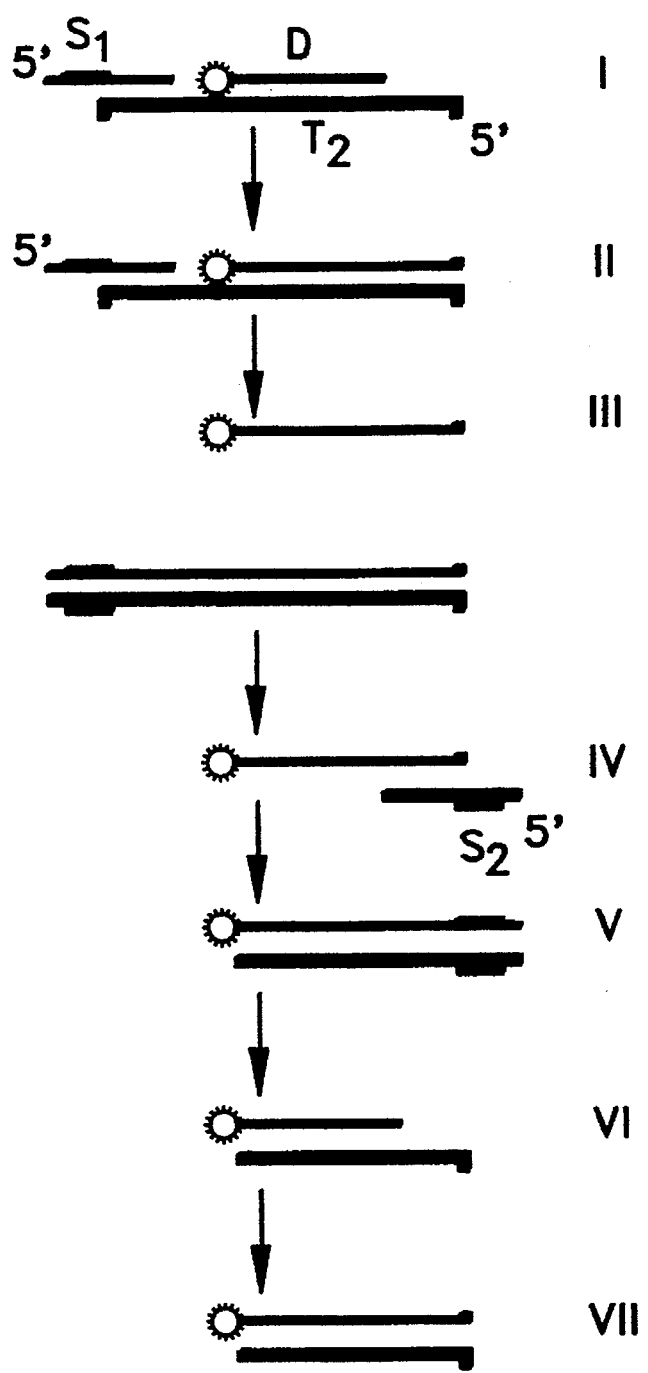
FIG. 2A illustrates the various forms of the fluorescent detector probe generated in a target-dependent manner during SDA when the detector probe is entirely homologous to the target sequence.
Figure 2B:
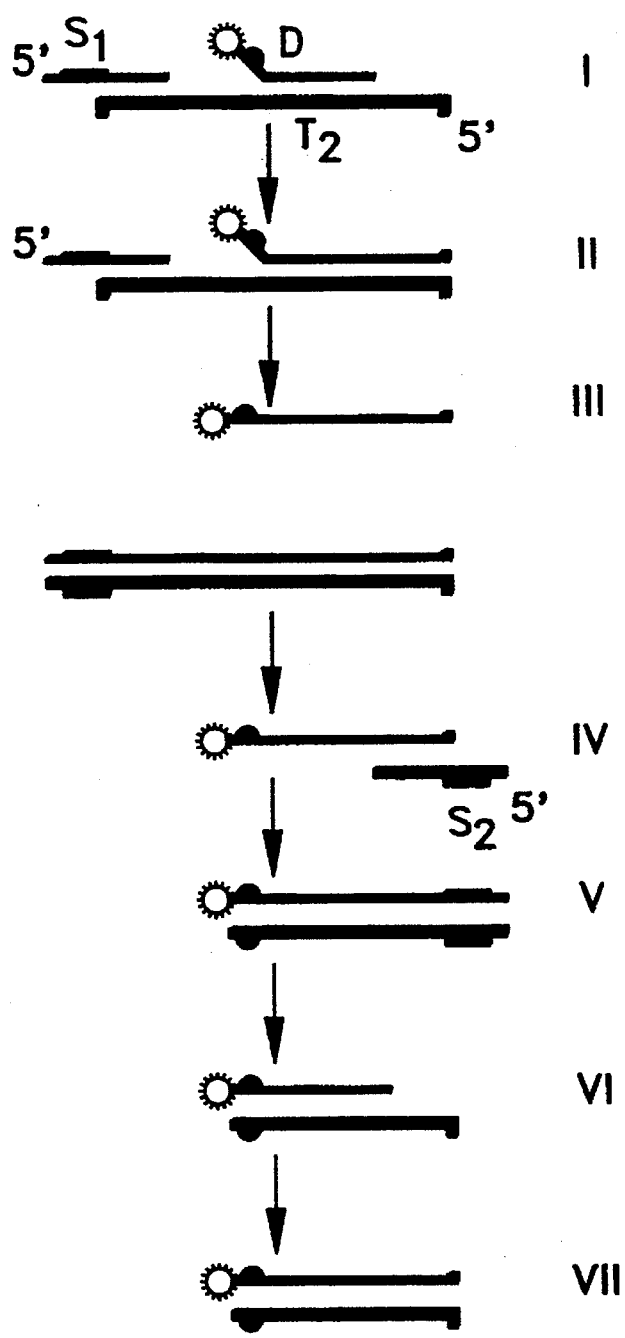
FIG. 2B illustrates the various forms of the fluorescent detector probe generated in a target-dependent manner during SDA when the detector probe is partially homologous to the target sequence, e.g., when the detector probe contains a recognition site for a double-stranded DNA binding protein (i.e., the nucleotide sequence to which the DNA binding protein binds).

In the inventive amplification detection system, a single-stranded oligodeoxynucleotide detector probe comprising a fluorescent label is converted to double-stranded form in a target-dependent manner during SDA (FIG. 2A and FIG. 2B). FIG. 2A and FIG. 2B illustrate the same process, except that in FIG. 2A the entire nucleotide sequence of the detector probe is complementary to the target sequence and in FIG. 2B a portion of the nucleotide sequence of the detector probe is not complementary to the target sequence. As discussed below, the non-complementary portion of the detector probe may comprise a recognition site for a DNA binding protein or may be a structural feature which results in an increase in FP. In FIG. 2B, the non-complementary sequence or structural feature is depicted as ▃. In both FIG. 2A and FIG. 2B, the fluorescent label is depicted as ✪.

The following references to structures relate to both FIG. 2A and FIG. 2B. Hybridization, extension and displacement of a fluorescent detector probe for FP detection of amplification occurs concurrently with the SDA cycle shown on the right side of FIG. 1. The fluorescent detector probe (D) hybridizes to one of the two complementary strands of a double stranded target sequence or to a displaced single-stranded copy of the target strand downstream from one of the SDA primers (e.g., $S_1$). This provides one source of double-stranded detector probe (structure I). The amplification primer/target complex is identical to the complex shown at the top left of the SDA cycle illustrated on the right side of FIG. 1, but in FIG. 1 it is depicted without the detector probe. The primer and detector probe in structure I are then simultaneously extended by exo$^-$ Klenow polymerase (structure II), resulting in displacement of the detector probe extension product (structure III by extension of the upstream amplification primer $S_1$ in a manner analogous to the strand displacement reaction intrinsic to SDA. The displaced, single-stranded probe extension product (structure III) hybridizes to the other SDA primer ($S_2$) forming a complex (structure IV) which becomes fully double-stranded by exo$^-$ Klenow polymerase extension, again providing a source of double-stranded fluorescent detector probe (structure V). Structure V is a template for linear SDA, due to the nickable HincII site on $S_2$. Nicking, polymerase extension and strand displacement using structure V as a template produces single-strands to which additional fluorescent detector probes hybridize (structure VI) and are extended to generate structure VII. Structure I, structure II, structure V and structure VII are all forms of double-stranded fluorescent detector probe which are indicative of target-specific SDA. Each of these structures contributes in a target-dependent manner to the increase in FP associated with double-stranded conversion of the single-stranded fluorescent detector probe. FIG. 2B illustrates how this same process also results in conversion of the DNA binding protein recognition site or structural feature to double-stranded form (structures V, VI and VII). These structures may then bind the double-stranded DNA binding protein to enhance the increase in FP associated with double-strandedness of the detector probe.

Any protein which binds to a specific double-stranded DNA sequence may be used to enhance the increase in FP associated with conversion of the detector probe to double-stranded form. This is accomplished by including the nucleotide sequence of the appropriate recognition site for the double-stranded DNA binding protein in the nucleotide sequence of the detector probe at a position near the site of attachment of the fluorescent label. Recognition sites for restriction endonucleases (e.g., EcoRI and mutant forms of EcoRI) are useful for this purpose. In addition, the recognition site for the Trp repressor protein (i.e., the Trp repressor operator sequence) or the recognition sequence for the DNA binding domain of the estrogen receptor protein (i.e., the estrogen responsive element sequence) may be included in the sequence of the detector probe to enhance the increase in FP upon binding to Trp repressor or estrogen receptor. Changes in FP may also be enhanced by designing a detector probe comprising a nucleotide sequence which results in a structural feature which further slows the tumbling of double-stranded DNA, for example a recognition site for a third oligonucleotide which in double-stranded form is capable of hybridizing to the third oligonucleotide to form a triple helical structure.

It is not a requirement of the invention that the detector probe carry the fluorescent label, as in the foregoing illustrative example. It will be apparent to one skilled in the art that, in certain embodiments of the invention, the detector probe may be unlabeled. That is, if a double-stranded DNA binding protein is included to increase the magnitude of the difference in FP between single- and double-stranded forms, the fluorescent label may be linked to the double-stranded DNA binding protein rather than to the detector probe. Similarly, if formation of a triple helix is used to increase the magnitude of the change in FP, the fluorescent label may be linked to the third oligonucleotide which hybridizes to the double-stranded structure containing the unlabeled detector probe. In this embodiment, the presence of the unlabeled detector probe in the amplification reaction would result in unlabeled versions of structures V, VI, and VII (of FIG. 2B), produced in a target-dependent manner. As these structures contain double-stranded recognition sites for double-stranded DNA binding proteins or triple helix forming oligonucleotides, specific binding of the fluorescently labeled protein or oligonucleotide to double-stranded detector probe structures will increase the magnitude of the change in FP and provide the fluorescent label needed for detection by FP. As smaller double-stranded DNA binding agents have a greater effect on the change in FP, triple helix formation is likely to be a more sensitive detection system than protein binding in many cases.

FIG. 2A, FIG. 2B and the foregoing description of the invention use SDA as an example, however, the invention may also be applied to any amplification method in which a strand-displacing polymerase is used or can be substituted for a polymerase which has 5'-3' exonuclease activity. The ability of the polymerase to displace a downstream strand of DNA without digesting it is the essential feature of the amplification method which provides target-specific generation of double-stranded fluorescent detector probe. The other features of such amplification methods, such as the nature of the target sequence and the structural features of the amplification primers, are not critical to the present invention. The inventive methods may therefore be used in isothermal amplification reactions other than SDA, e.g., Self-Sustained Sequence Replication (3SR), as the detection method is independent of whether the target sequence is RNA or DNA. In 3 SR, target-dependent generation of double-stranded detector probe occurs generally as illustrated in FIG. 2A and 2B for SDA. The T7 RNA polymerase lacks 5'-3' exonuclease activity. The degradative activity of reverse transcriptase is an RNAse H activity which is active only on RNA hybridized to DNA. In the 3 SR amplification scheme of Guatelli, et al. (1990. 87, 1874–1878. See FIG. 1), the detector probe of the invention hybridizes to the RNA target sequence and is displaced by extension of the 3' amplification primer "A". The detector probe also hybridizes to the DNA target sequences generated in the 3SR amplification process. In either case, the extended detector probe is displaced by the polymerase when the upstream 3' ("A") or 5' ("B") amplification primer is extended. The opposite amplification primer then binds to the detector probe extension product and is extended, converting the fluorescently-labeled detector probe to double-stranded form. Detector probe extension products which include the T7 RNA polymerase promoter sequence are amplifiable by 3SR and provide a source of additional copies of the detector probe.

The inventive methods may also be applied to monitoring of the Polymerase Chain Reaction (PCR), although fluorescence polarization measurements must be taken during the low temperature periods of the amplification cycle for "real time" monitoring of amplification. Again, the mechanism for target-dependent generation of double-stranded detector probe is generally as illustrated in FIG. 2A and 2B. Using a 5'-3' exonuclease deficient polymerase (e.g., exo$^-$ Klenow, Bca polymerase or Bst polymerase), extension of a PCR amplification primer hybridized to the target sequence displaces the extended downstream detector probe. The opposite PCR amplification primer hybridizes to the extension product of the detector probe and is extended, resulting in conversion of the single-stranded detector probe to double-stranded form. The double-stranded detector probe is amplifiable by hybridization and extension of one amplification primers and one detector probe in subsequent cycles, providing an additional source of double-stranded detector probe. The increase in fluorescence polarization or fluorescence anisotropy may then be detected after conclusion of the PCR under conditions in which amplification products remain double-stranded or during PCR at the low temperature points of the cycling protocol.

Single- to double-stranded conversion of the detector probe is monitored by measuring fluorescence polarization or fluorescence anisotropy. The change in exclusion volume which accompanies the change in probe conformation (primarily strandedness) results in a detectable increase in correlation time (tumbling time) for the fluorescent label. The accompanying changes in FP values may be monitored on a transient-state fluorometer (e.g., from Diatron) or a steady state fluorometer (e.g., Jolley Instruments) designed for detection of the selected fluorescent label. While the polarization measurements may be taken post-amplification, as has been done previously, the present methods also for the first time allow "real-time" monitoring of fluorescence polarization during target sequence amplification. Real-time monitoring of fluorescence provides significant advantages over the prior art. That is, it provides an essentially immediate result, it is quantitative, it improves sensitivity (analysis of a change in slope is more accurate than a single endpoint), and the sample acts as its own internal standard. This last advantage is particularly important for analysis of clinical specimens, as sample viscosity may significantly affect endpoint readings.

As hybridized and unhybridized (i.e., double and single stranded) probe are not separated prior to measurement, FP-based detection of target amplification requires appreciable conversion of the single-stranded fluorescent detector probe to double-stranded form. Therefore, low detector probe concentrations facilitate high sensitivity (i.e., detection of amplification of initially low concentrations of target sequence) because they result in a higher percentage of converted detector probe for a given level of target amplification. However, low detector probe concentrations present a kinetic challenge for SDA. The fluorescent detector probe must hybridize to the displaced target strand before hybridization and extension of the upstream amplification primer ($S_1$). The kinetics of $S_1$ extension are controlled by $S_1$ hybridization and polymerase binding rates. It is therefore useful in some cases to modify conventional SDA reaction conditions (Walker et al. 1992. *Proc. Natl. Acad. Sci. and Nucl. Acids Res., supra*; Walker. 1993. *PCR Methods and Applications* 3, 1–6) to decrease the rate of $S_1$ extension and facilitate prior hybridization of the fluorescent detector probe when low target concentrations are present. This may be achieved by adjusting the concentration of $S_1$ and polymerase to 10 nM–1 µM and 0.1–10 unit, respectively. Lower $S_1$ and polymerase concentrations result in slower SDA rates, so it may also be necessary to extend the typical SDA reaction time from 2 to 3 hours. If sensitivity is not essential, or for quantitation of relatively high initial target concentrations, the fluorescent detector probe concentration may be as high as the concentration of amplification primer.

Use of an unlabeled detector probe, as described above, may be employed in the amplification reaction to allow rapid extension of the $S_1$ primer even when it is desired to keep the concentration of fluorescently-labeled probe low, e.g., for increased sensitivity. In this embodiment, the detector probe is not fluorescently labeled but includes near its 5' end a sequence which, in double-stranded form, is capable of hybridizing to a fluorescently labeled third oligonucleotide to form a triple helix. Conversion of the unlabeled detector probe to double-stranded form (following the reaction scheme of FIG. 2B—structures V, VI and VII) allows hybridization to the fluorescently labeled third oligonucleotide for detection of the associated increase in FP. The unlabeled detector probe can be present in the amplification reaction at concentrations comparable to $S_1$ so that reaction kinetics are improved and its rate of conversion to structure V, VI or VII is more rapid. Once these target-specific double-stranded structures are formed during amplification, the fluorescently labeled third oligonucleotide probe hybridizes, enhancing the increase in FP and providing the fluorescent label for specific detection. The third oligonucleotide with its fluorescent label may be present at high or low concentration depending on the sensitivity required, without interfering with the efficiency of production of double-stranded detector probe products. In addition, in this embodiment the fluorescent label may be linked to the 3' end of the third oligonucleotide if desired, a configuration which is not desirable when the label is linked to the detector probe.

The processes illustrated in FIG. 2A and FIG. 2B occur concurrently with the SDA cycle depicted in FIG. 1, without interfering with the amplification reaction. The presence of the fluorescent detector probe does not increase SDA background reactions because any mispriming by the detector probe and an amplification primer generates an extension product which cannot be exponentially amplified due to the presence of only one nickable HincII site (i.e., the fluorescent detector probe does not contain a nickable HincII site). SDA requires two primers, each containing a nickable HincII site, to support exponential amplification. This is in contrast to the Polymerase Chain Reaction, in which any oligonucleotide which hybridizes to any sequence and can be extended serves as an amplification primer, allowing ntisprimed products to be exponentially amplified. Background amplification in SDA is further reduced when the fluorescent detector probe is used at low concentrations (e.g., 50 pM–10 nM).

Any fluorescent molecule known in the art for labeling nucleic acids may be used in the methods of the invention (e.g., fluorescein and fluorescein derivatives such as eosin; rhodamines such as Texas Red and tetramethylrhodamine; cyanine dyes such as thiazole orange, oxazole yellow and related dyes described in U.S. Pat. Nos. 4,957,870 and 4,888,867; pyrene; porphyrin dyes such as La Jolla Blue™). The fluorescent label should be selected such that the fluorescent lifetime of the label is comparable in magnitude to the correlation time being measured, taking into account that temperature, viscosity, and the size of the oligonucleotide to which the fluorescent dye is conjugated all affect tumbling time. For example, fluorescein (lifetime approximately 4 nanosec.) and LaJolla Blue™ (lifetime approximately 2 nanosec.) are both useful for correlation times of about 0.1–100 nanosec. If a nucleic acid binding protein is used in conjunction with the fluorescent label, the correlation time measured is generally increased. For example, correlation time for a free fluorescein label is about 0.2 nanosec. The correlation time increases to about 0.4 nanosec. when the fluorescein label is conjugated to a single stranded oligonucleotide and increases further to about 2 nanosec. when conjugated to a double-stranded oligonucleotide. When FP is enhanced by binding the fluorescein-labeled double-stranded oligonucleotide with EcoRI, the correlation time again increases to about 20 nanosec. La Jolla Blue™ (Devlin, et al. 1993. *Clin. Chem.* 39, 1939–1943) is particularly suitable for labeling the fluorescent detector probe when biological samples are to be amplified, as this dye absorbs and emits light in the near-infra red spectrum, a region of relatively low background fluorescence with clinical specimens (peak maxima at about 685 nm and 705 nm, respectively).

Background fluorescence may be further minimized by the use of transient-state fluorescence spectroscopy rather than steady-state fluorescence spectroscopy, thereby reducing the contribution from light scattering. Lower background fluorescence allows the use of lower concentrations of fluorescently labelled detector probe, which improves detection sensitivity by ensuring that a greater percentage of single-stranded detector probe is converted to double-stranded form for a given concentration of amplified product. However, low detector probe concentrations result in saturation of the detector probe over a broad range of amplified product levels. End-point measurements of FP taken under conditions of probe saturation after completion of SDA may not be strictly quantitative with regard to the initial target levels. Monitoring FP in "real-time," during SDA rather than after completion of the amplification reaction, overcomes the problem of detector probe saturation because samples containing higher target levels exhibit more rapid increases in FP values than those containing less target. Of course, the correlation between the rate of FP increase and initial target levels is valid only when comparing samples in which the rate of amplification is essentially identical. Again, for clinical specimens, each of which contains varying levels of SDA inhibitors, the assay may not be strictly quantitative. For example, it may be difficult to differentiate a sample which contains a high amount of initial target and undergoes inefficient SDA from a sample which contains a low amount of initial target but undergoes SDA at a high rate. Nevertheless, realtime monitoring of FP values during SDA provides at least a semi-quantitative estimate of initial target levels. Quantitation may be improved by including an additional target sequence at a known initial concentration as a positive control (Walker, et al. 1994. *Nucl. Acids Res.* 22, 2670–2677). The positive control target not only provides an indication of general SDA performance for a sample (i.e., a control for false negatives), it also provides a standard for quantitating the initial amount of target in the sample.

The fluorescent label is covalently linked or conjugated to the detector probe so as not to interfere with either emission of fluorescence from the label or hybridization of the probe to the target sequence. As FP changes occur when the label is near or involved in a conformational change, the linkage should be in proximity to the site where the conformational change is expected. This may be either the 5' end of the detector probe or an internal site. In general, the label is not linked to the 3' end of the detector probe, as the 3' end must be available for extension by polymerase. A more rigid linkage or "tether", such as one containing double bonds, slows the tumbling time of the fluorescent label and allows measurement of longer correlation times. The fluorescent label is covalently coupled to the detector probe via a linker or "tether" suitable for use in conjugating labels to oligonucleotides, e.g., amino-ethyl, amino-hexyl and amino-propyl linking arms (Applied Biosystems, Clontech, Glen Research, Devlin, et al., supra.). Other amino linkers are described in WO 92/18650. The label may also be conjugated to the oligonucleotide at C5 of pyrimidines or C8 of purines, as generally described by Goodchild, 1990. *Bioconj. Chem.* 1, 165. Fluorescein may be linked internally by synthesis of an oligonucleotide containing a phosphorothioate, and subsequent reaction with iodoacetamidofluorescein.

FP may be used for detection of amplification of any target for which appropriate amplification primers and detector probes can be designed. In one representative embodiment, the inventive detection methods may be applied to an SDA system previously developed for amplification of an *M. tuberculosis* target sequence (IS6110 - Walker et al. 1992. *Nucl. Acids Res.* and *Proc. Natl. Acad. Sci., supra*; Spargo et al. 1993, supra). Samples containing different amounts of *M. tuberculosis* genomic DNA (which includes the IS6110 target sequence) and a fluorescent detector probe were amplified and amplification was simultaneously detected by the increase in FP. The two samples containing target *M. tuberculosis* DNA exhibited an increase in FP values over time while the negative control (zero *M. tuberculosis* DNA) did not display any significant change in FP values. Furthermore, the samples containing *M. tuberculosis* DNA exhibited increasing FP values in a time dependent fashion which reflected initial *M. tuberculosis* target levels (i.e., quantitative detection). This experiment illustrated the utility of the system for real-time detection of SDA. However, the current design of the Diatron fluorometer used for detection of FP rendered careful execution of SDA reactions in the fluorometer logistically difficult. Specifically, sample temperature control on the current Diatron instrument was not optimum for the SDA reaction. Consequently, SDA was also performed in the presence of the detector probe in microcentrifuge tubes using a temperature controlled water bath, with subsequent measurement of FP values in the fluorometer. Samples containing *M. tuberculosis* DNA exhibited detectably higher FP values than the samples lacking *M. tuberculosis* DNA even when only 1 *M. tuberculosis* genome was present as a target. Although FP values generally increased with increasing levels of initial *M. tuberculosis* DNA, FP values tended to reach a maximum level over a range of target input levels. This was due to the low concentration of detector probe used to increase sensitivity, which resulted in complete conversion of the detector probe to double-stranded form (probe saturation).

Samples which truly lacked *M. tuberculosis* target DNA exhibited FP values characteristic of single-stranded detector probe (in this case, about 40–45 mP for fluorescein and about 60 mP for La Jolla Blue™—"LJB"). Any observed increase in FP values for these zero target samples may theoretically derive from two sources. First, there may have been accidental contamination with minute quantities of target DNA. Low level contamination of negative samples with even a few target molecules is a concern with amplification techniques like SDA because they are powerful enough to allow detection of very few target molecules. Second, the detector probe in zero target samples may be converted to double-stranded form directly through background hybridization (e.g., to the human DNA which is often present in test samples) or through spurious polymerase activity such as extension of a transiently formed hairpin in the detector probe. Two types of control samples have been analyzed to elucidate possible sources of background signal in zero target samples. One type of control sample contained dATP instead of dATPαS in the SDA reaction. Substitution of dATP allowed any nonspecific extension of the detector probe by exo⁻ Klenow, but disabled the SDA mechanism by allowing double-stranded cleavage of HincII sites. The second type of control sample did not contain exo⁻ Klenow. This disabled both SDA and any nonspecific detector probe extension. Controls without polymerase therefore revealed any nonspecific, direct hybridization of the detector probe with non-target DNA. Analysis of these control samples and the zero target samples indicated that nonspecific hybridization of the detector probe is extremely low and not mediated by exo⁻ Klenow. The slightly higher FP values which may be recorded upon amplification of zero target samples probably reflect minute contamination with target DNA.

The following experimental examples are provided to illustrate certain embodiments of the invention but are not intended to limit the invention as defined by the appended claims. The sequences of the oligonucleotides used in the examples are as follows:

| OLIGONUCLEOTIDE SEQUENCE | SEQ ID NO: |
| --- | --- |
| 5'dGCATTATAGTACCTGTCT*GTTGA*CACTGAGATCCCCT3' | SEQ ID NO: 1 |
| 5'dTTGAATAGTCGGTTACTT*GTTGA*CGGCGTACTCGACC3' | SEQ ID NO: 2 |
| 5'dTGGACCCGCCAAC3' | SEQ ID NO: 3 |
| 5'dCGCTGAACCGGAT3' | SEQ ID NO: 4 |
| 5'LJB-dTGAAAGACGTTATCCACCATACGGATAG3' | SEQ ID NO: 5 |
| 5'F-dG*GAATTC*ATCCGTATGGTGGATAACGTCTTTCA3' | SEQ ID NO: 6 |
| 5'F-dATCCGTATGGTGGATAACGTCTTTCA3' | SEQ ID NO: 7 |
| 5'dTGAAAGACGACGTTATCCACCATACGGAT*GAATTC*C3' | SEQ ID NO: 8 |
| 5'dTGAAAGACGTTATCCACCATACGGAT3' | SEQ ID NO: 9 | wherein LJB indicates conjugation of the oligonucleotide to La Jolla Blue™, F indicates conjugation of the oligonucleotide to fluorescein, and italics indicate the HincII recognition site (5'GTTGAC) or the EcoRI recognition site (5'GAATTC). SEQ ID NO: 6 and SEQ ID NO: 8 are complements. SEQ ID NO: 7 and SEQ ID NO: 9 are also complementary.

EXAMPLE 1

FP values were monitored in real-time during SDA of samples containing M. tuberculosis target DNA and a La Jolla Blue™ labelled detector probe (SEQ ID NO: 5). SDA reaction conditions were modified to improve sensitivity as described above and dUTP was substituted for TTP to allow subsequent inactivation of amplicons using UDG. Each 120 µL sample contained 50 mM $K_2PO_4$ (pH 7.6), 7 mM $MgCl_2$, 0.5 mM dUTP, 0.2 mM each dGTP, dCTP and dATPαS, 16% (v/v) glycerol, 0.1 mg/mL BSA, 0.001% Tween-20, 100 ng human placental DNA, 100 nM primer $S_1$ (SEQ ID NO:2), 300 nM primer $S_2$ (SEQ ID NO:1), 25 nM each primers $B_1$ and $B_2$ (SEQ ID NO:3 and SEQ ID NO:4), 300 units HincII (New England Biolabs), 0.25 units exo⁻ Klenow (United States Biochemical), 500 pM La Jolla Blue™ labelled detector probe (SEQ ID NO: 5) and the amounts of M. tuberculosis genomic DNA indicated in FIG. 3. The reactions in this example correspond to FIG. 2, with the detector probe hybridizing downstream of $S_1$.

La Jolla Blue™ was conjugated to the 5'-end of the oligodeoxynucleotide detector probe as previously described (Devlin, et al., supra). This detector probe hybridizes to nucleotide positions 985–1012 of the IS6110 element found in the M. tuberculosis genome (Nucl. Acids Res. 1990. 18, 188). The site of detector probe hybridization is contained in the target sequence being amplified (nucleotide positions 972–1023). For each sample, all reagents except HincII and exo⁻ Klenow were assembled in a microcentrifuge tube, the sample was heated in a boiling water bath for 2 minutes and then equilibrated at 40° C. in a water bath. The samples were transferred to glass cylindrical cuvettes (4 mm inner diameter, 23 mm height), equilibrated at 40° C. in the fluorometer, and HincII and exo⁻ Klenow were added. Fluorescence polarization values were recorded (Devlin et. al. 1993, supra) as SDA proceeded at 40° C.

Figure 3:
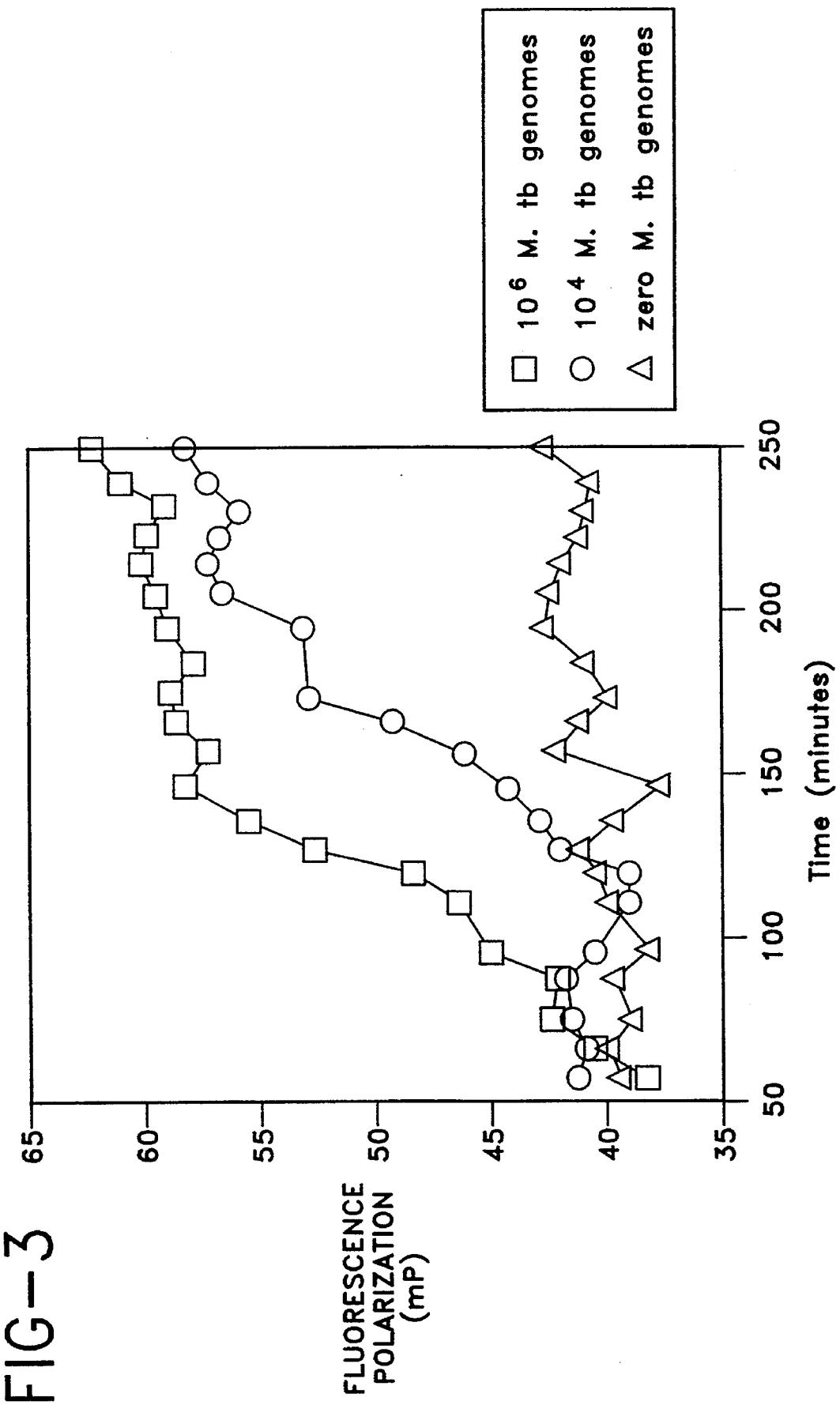
FIG. 3 is a graph of the increase in FP associated with SDA of an *M. tuberculosis* target sequence.

In this experiment, SDA was performed in the Diatron transient state fluorometer. FP values were recorded as a function of time for the three samples containing the indicated amount of target DNA. FP values were expressed as millipolarization units (mP): FP (mP)=1000[S(par)-S(perp)]/[S(par)+S(perp)]. S(par) and S(perp) represent the total number of counts over a portion of the fluorescence decay curve where the transient-state fluorescence signal has the highest signal-to-noise ratio with the emission polarizer in the parallel (par) and perpendicular (perp) positions, respectively. FIG. 3 is a plot of FP values as a function of time. Single- to double-stranded conversion of the detector probe, as evidenced by increasing fluorescence polarization values, was found to be dependent upon the initial concentration of M. tuberculosis DNA. Samples containing higher initial levels of target converted more rapidly than those containing lower initial levels or target. In contrast, the sample lacking M. tuberculosis target DNA exhibited no substantial increase in FP values.

EXAMPLE 2

SDA reactions were performed as described in Example 1, but FP values were measured after termination of SDA. The La Jolla Blue™ detector probe (SEQ ID NO: 5) was present during SDA at 500 or 50 pM. SDA proceeded for 3 hours in microcentrifuge tubes maintained at 41° C. in a water bath and was terminated by addition of EDTA to 8 mM. The samples were transferred to glass cylindrical cuvettes (4 mm inner diameter, 23 mm height) and read on a Diatron transient-state fluorometer. FP values (mP) were taken for samples containing various levels of input target M. tuberculosis DNA. Two additional control reactions were also included. One incorporated dATP instead of dATPαS during SDA, which supports general enzyme activity for HincII and exo⁻ Klenow but does not support amplification of the target. The second control lacked exo⁻ Klenow.

Figure 4:
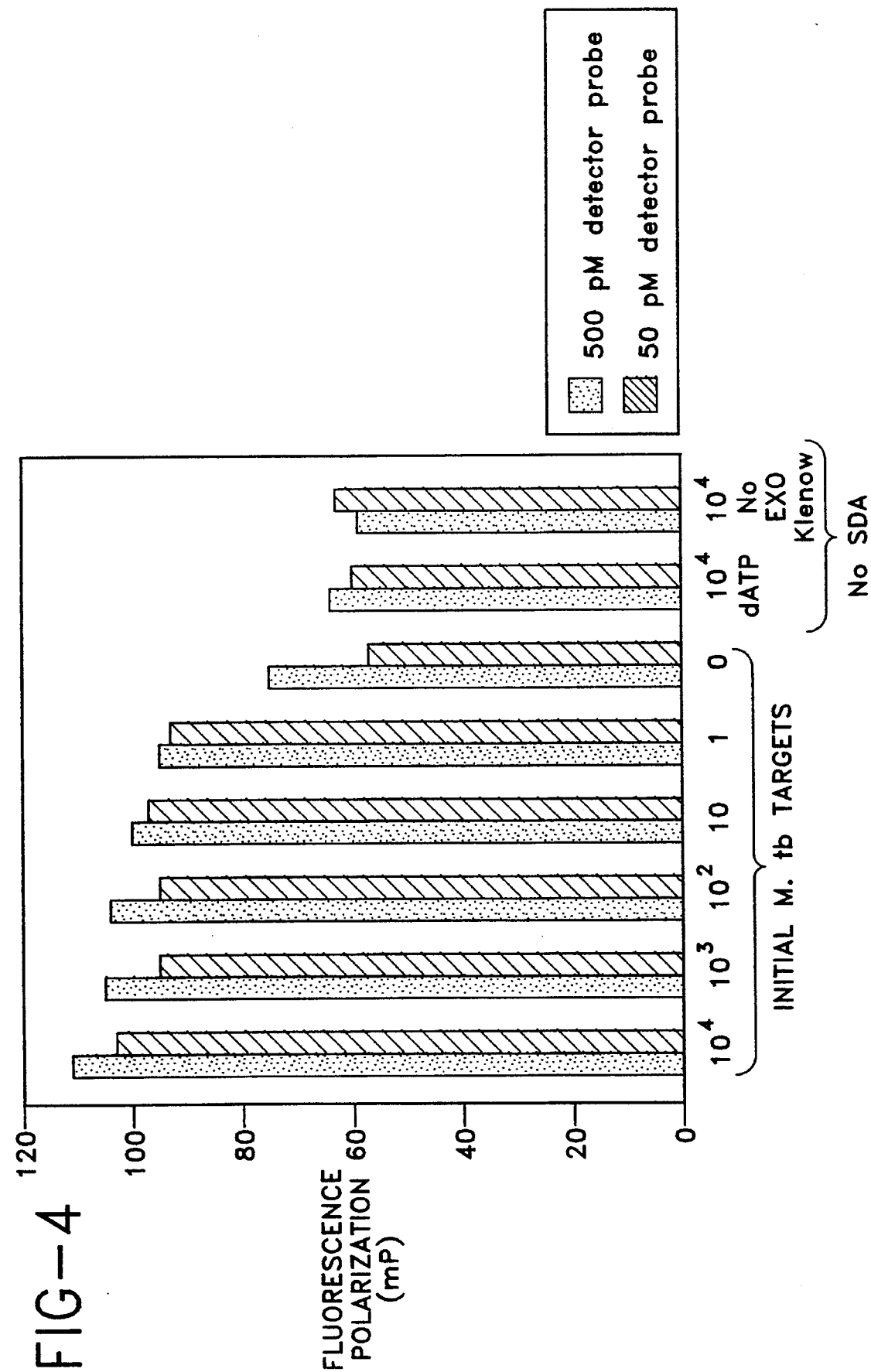
FIG. 4 is a graph of fluorescence polarization values obtained after SDA of various initial amounts of an *M. tuberculosis* target sequence.

The results, after completion of SDA, are shown in FIG. 4. All samples containing M. tuberculosis target DNA exhibited higher FP values than the samples lacking M. tuberculosis DNA due to target-dependent single- to double-stranded conversion of the La Jolla Blue™ labelled detector probe during SDA. With 500 pM of detector probe, there was a trend toward decreasing magnitude of the change in FP values with decreasing levels of M. tuberculosis DNA. This decrease in magnitude, if any, was minimal with 50 pM of detector probe, suggesting probe saturation. However, the poor signal to noise ratio obtained with the lower detector probe concentration also compromises accuracy. The zero M. tuberculosis DNA samples, with 500 pM detector probe, displayed FP values slightly higher than the two control samples ("dATP" and "no exo⁻ Klenow"), probably due to accidental contamination with minute quantities of the IS6110 target sequence. IS6110 is present in about 10 copies per M tuberculosis genome, an amount of target sequence which is amplifiable by SDA even if only one contaminating genome is present. Analysis of the two control reactions indicated that the polymerase did not convert single-stranded detector probe to double-stranded form in a non-target specific manner, as evidenced by equal fluorescence polarization values for the sample containing dATP in place of dATPαS and the sample lacking exo⁻ Klenow.

EXAMPLE 3

5'-Fluorescein labeled oligonucleotides were prepared by standard procedures using an Applied Biosystems, Inc (ABI)

Model 380B DNA Synthesizer and ABI 6-FAM Amiditc (P/N 401527) according to the instructions of the manufacturer. Fluorescein labeled oligonucleotides were purified by denaturing gel electrophoresis. FP values for fluorescein were recorded on an FPM 1 steady state fluorometer from Jolley Consulting and Research, Inc., 34469 N. Circle Dr., Round Lake, IL 60073. This instrument uses disposable 12×75 mm test tubes (Fisher) with a minimum sample volume of 1 mL.

EXAMPLE 4

Figure 5:
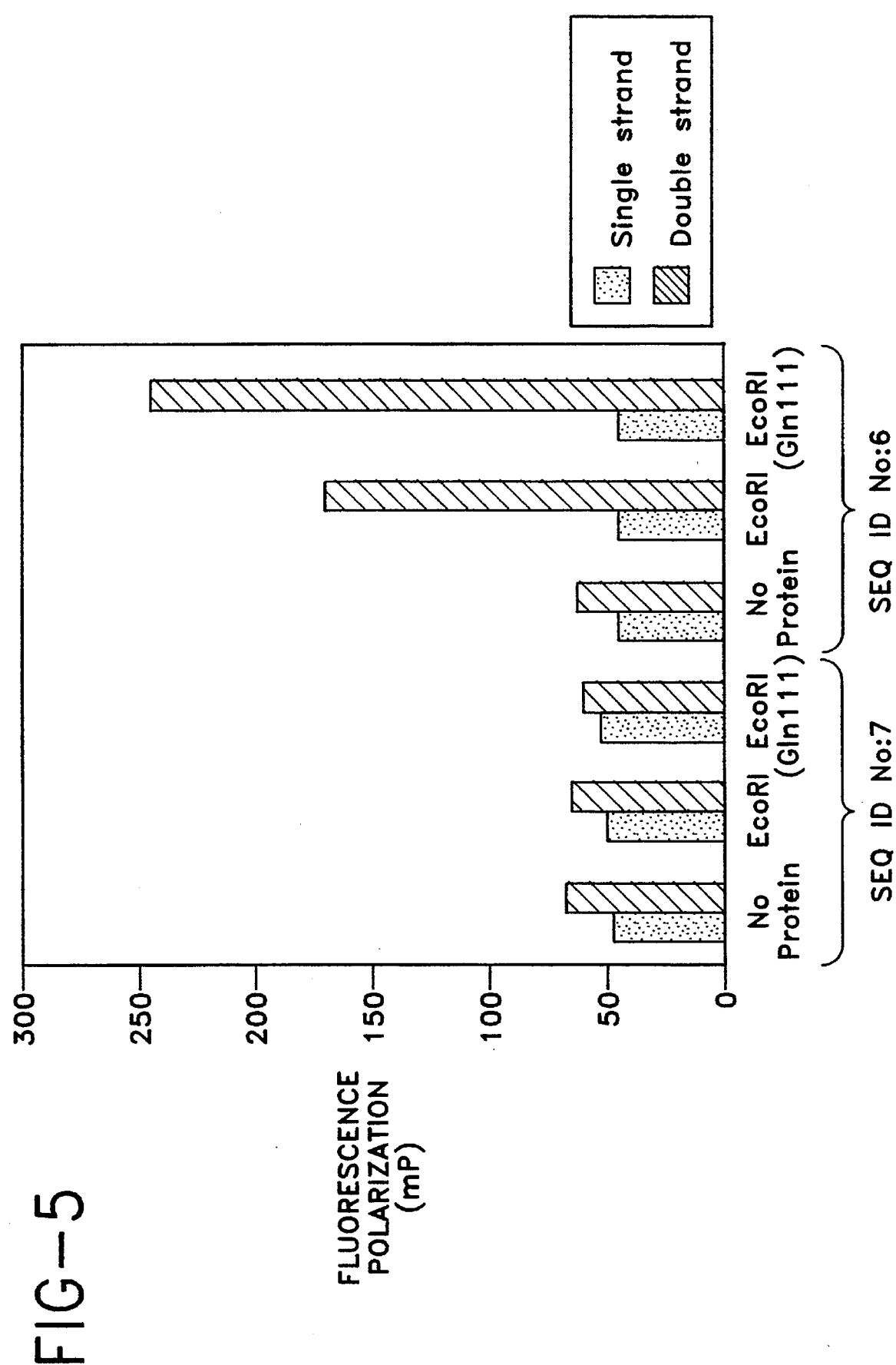
FIG. 5 is a graph showing enhancement of the increase in FP by addition of EcoRI or EcoRI (Gln 111) when a single-stranded oligonucleotide is converted to double-stranded form by hybridization to its complement.

Samples (100 µL) of 10 nM SEQ ID NO: 6 with or without 10 nM SEQ ID NO: 8 (the complement of SEQ ID NO: 6) were prepared in 4mM TAE, 50 mM NaCl, pH 7.8. Control samples, containing oligonucleotides which lacked an EcoRI recognition site, were similarly constructed using SEQ ID NO: 7 with and without its complement (SEQ ID NO: 9). These samples were incubated for 30 minutes at 37° C. and then diluted to 1 mL using 55 mM NaCl, 22 mM TRIS-HCl (pH 7.5), 0.7 mM $K_2PO_4$ (pH 7.4), 1.1 mM EDTA, 0.7 mM beta mercaptoethanol, 13 µg/mL BSA, 0.02% Triton X-100, 7% glycerol. FP values were recorded at 37° C. on the FPM-1 instrument. Then 5 µL of 100,000 units/mL EcoRI (New England BioLabs) or 5 µL of 1.6 gM EcoRI (Gln 111) were added, and FP readings were taken at the indicated times. The results, 1 hour post-addition of DNA binding protein, are shown in FIG. 5.

FP values increased from 45.6 to 64.1 mP upon hybridization of SEQ ID NO: 6 to its complement (SEQ ID NO: 8), corresponding to a change of 18 mP. Inclusion of EcoRI increased the change in FP accompanying the conformational transition from 18 mP to 133 mP (181.2−48.2=133 mP). EcoRI (Gln 111) enhanced the increase in FP by 185 mP (242.1−57.3=185 mP). Not only did EcoRI (Gln 111) enhance the increase in FP to a greater extent than EcoRI, FP was stable over a longer period of time. This effect may be due to the tighter binding of EcoRI (Gln 111), resulting in relatively less dissociation of the protein from its recognition site as compared to EcoRI. In contrast, addition of the double-stranded DNA binding protein did not enhance the increase in FP associated with conversion from single- to double-stranded conformation when no recognition site for the protein was present (SEQ ID NO: 7).

EXAMPLE 5

SDA was performed in the presence of fluorescent detector probes (SEQ ID NO:6 or SEQ ID NO:7) on samples containing *M. tuberculosis* DNA. SEQ ID NO:7 has the same target binding sequence as SEQ ID NO:6, but lacks the EcoRI binding site present in SEQ ID NO:6. FP values were measured after completion of the SDA reaction, before and after addition of EcoRI or EcoRI (Gln 111). Both double-stranded DNA binding proteins were added to the sample containing SEQ ID NO: 7. SEQ ID NO: 6 and SEQ ID NO: 7 hybridize to nucleotide positions 985–1010 of the IS6110 element which is contained in the sequence undergoing SDA (nucleotide positions 972–1023). SDA reactions (100 µL) were generally performed as in Example 2 but with the following exceptions: SEQ ID NO: 7 or SEQ ID NO. 6 were included at 10 nM in place of SEQ ID NO: 5. The concentrations of $S_1$ (SEQ ID NO:2) and $S_2$ (SEQ ID NO:1) were 300 and 50 nM, respectively. In this example, in contrast to Example 1 and the illustration of the invention in FIG. 2, hybridization of the detector probe was downstream from $S_2$. Also, 1 unit of exo$^-$ Klenow was used. Each SDA reaction contained $10^6$ *M. tuberculosis* genomes, but 10 mM EDTA was added to some samples to inhibit SDA ("no SDA" controls). Following SDA, the samples were diluted as in Example 4 to 1 mL in disposable 12×75 mm glass tubes (Fisher) and incubated for 20 minutes at 37° C. before recording FP values on the FPM 1 instrument at 37° C. Following the initial FP reading, 5 µL of 100,000 units/mL EcoRI or 5 µL of 1.6 µM EcoRI (Gln 111) were added. The samples were then incubated at 37° C., and FP values were recorded.

Figure 6:
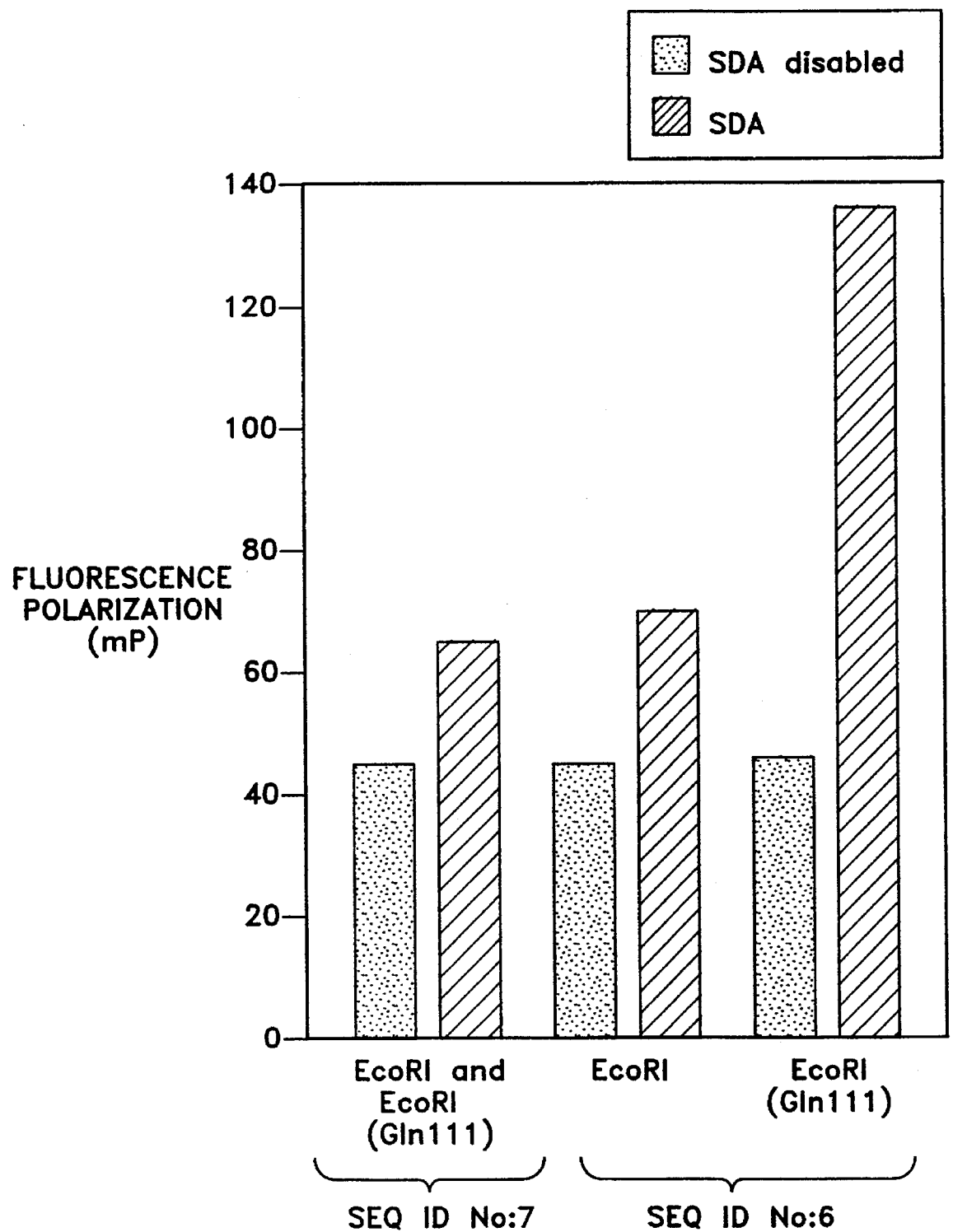
FIG. 6 is a graph showing enhancement of the increase in FP by addition of EcoRI (Gln 111) when the detector probe is converted to double stranded form during amplification of a target sequence.

The results, 2 hours post-addition of the double-stranded DNA binding protein, are shown in FIG. 6. SDA of *M. tuberculosis* DNA was observed as an increase in FP values for SEQ ID NO: 6 and SEQ ID NO: 7 before protein addition, indicating conversion to double-stranded form. FP values for the control, SEQ ID NO:7, increased from 21.3 mP upon SDA of the target *M. tuberculosis* sequence. Addition of EcoRI (Gln 111) increased the magnitude of the difference in FP between single-stranded and double-stranded forms to 89.4 mP for amplified samples containing SEQ ID NO:6 (in which a double-stranded EcoRI recognition site is generated). No such effect was observed upon addition of EcoRI (Gln 111) to amplified samples containing SEQ ID NO:7. In unamplified samples (in which the EcoRI site remained single-stranded) addition of EcoRI (Gln 111) did not result in any increase in FP over values expected for single-stranded probe alone. Compared to Example 4, which analyzed only the effect of binding of EcoRI and EcoRI (Gln 111 ), longer incubation with EcoRI (Gln 111) was required in this experiment to observe the enhanced increase in FP values. This may be due to some inhibition of the protein binding process under the conditions of SDA. In contrast to Example 4, EcoRI did not enhance the increase in FP values upon SDA amplification of SEQ ID NO:6 in spite of the double-stranded EcoRI binding site.

EXAMPLE 6

Figure 7:
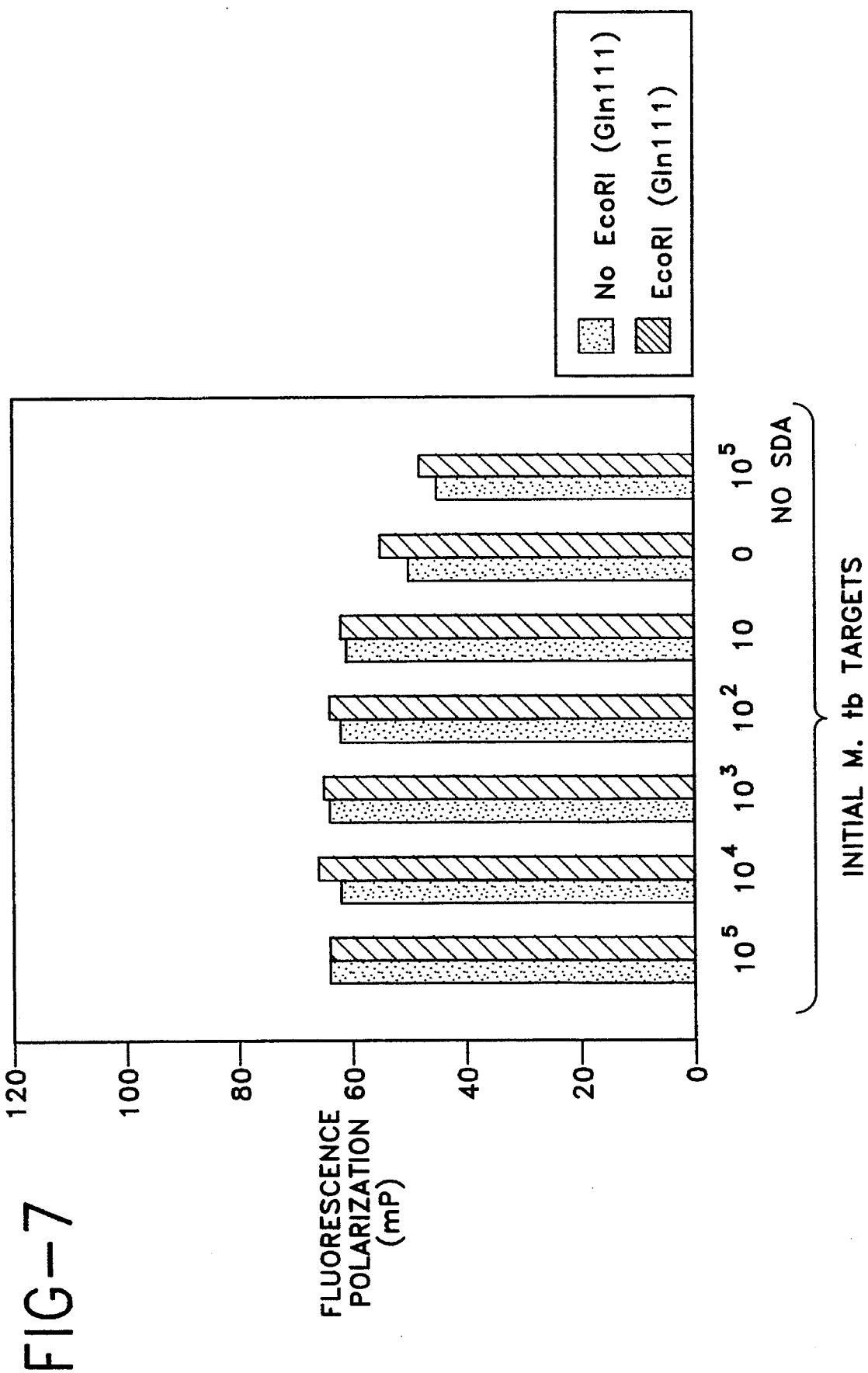
FIG. 7 is a graph illustrating FP values obtained upon amplification of various initial amounts of target sequence with post-amplification addition of EcoRI (Gln 111), using a detector probe which does not contain an EcoRI recognition site.

SDA was performed with SEQ ID NO: 6 or SEQ ID NO: 7 detector probes as in Example 5. The series of samples contained varying levels of *M. tuberculosis* target DNA with post-SDA addition of EcoRI (Gln 111). As previously noted, the SEQ ID NO: 7 detector probe has no EcoRI recognition site and should not bind EcoRI (Gln 111). A control SDA reaction which included 100,000 *M. tuberculosis* genomes and dATP instead of dATPαS was also performed. Following SDA, these 100 µL samples were diluted to 1 mL with buffers as in Example 4 and incubated at 37° C. for 20 minutes. FP values were recorded on the FPM 1 instrument. After the initial FP readings, 5 µL of 1.6 µM EcoRI (Gln 111) were added, and FP readings were recorded. The results for SEQ ID NO: 7, at 1.5 hours post-addition of double-stranded DNA binding protein, are shown in FIG. 7. The results for SEQ ID NO: 6, at 3.5 hours post-addition, are shown in FIG. 8.

For both SEQ ID NO: 6 and SEQ ID NO: 7, higher FP values were observed for all samples containing *M. tuberculosis* DNA as compared with the zero *M. tuberculosis* DNA sample before addition of EcoRI (Gln 111). The slightly higher FP values for the zero *M. tuberculosis* DNA samples compared with the negative control samples containing dATP instead of dATPαS ("no SDA" in FIG. 7 and FIG. 8) suggested that the zero *M. tuberculosis* samples were slightly contaminated with a few target molecules. Addition of EcoRI (Gln 111 ) enhanced the sensitivity of *M. tuberculosis* detection for SEQ ID NO: 6 (FIG. 8) but not SEQ ID NO: 7 (FIG. 7), which has no EcoRI recognition site.

EXAMPLE 7

Figure 9:
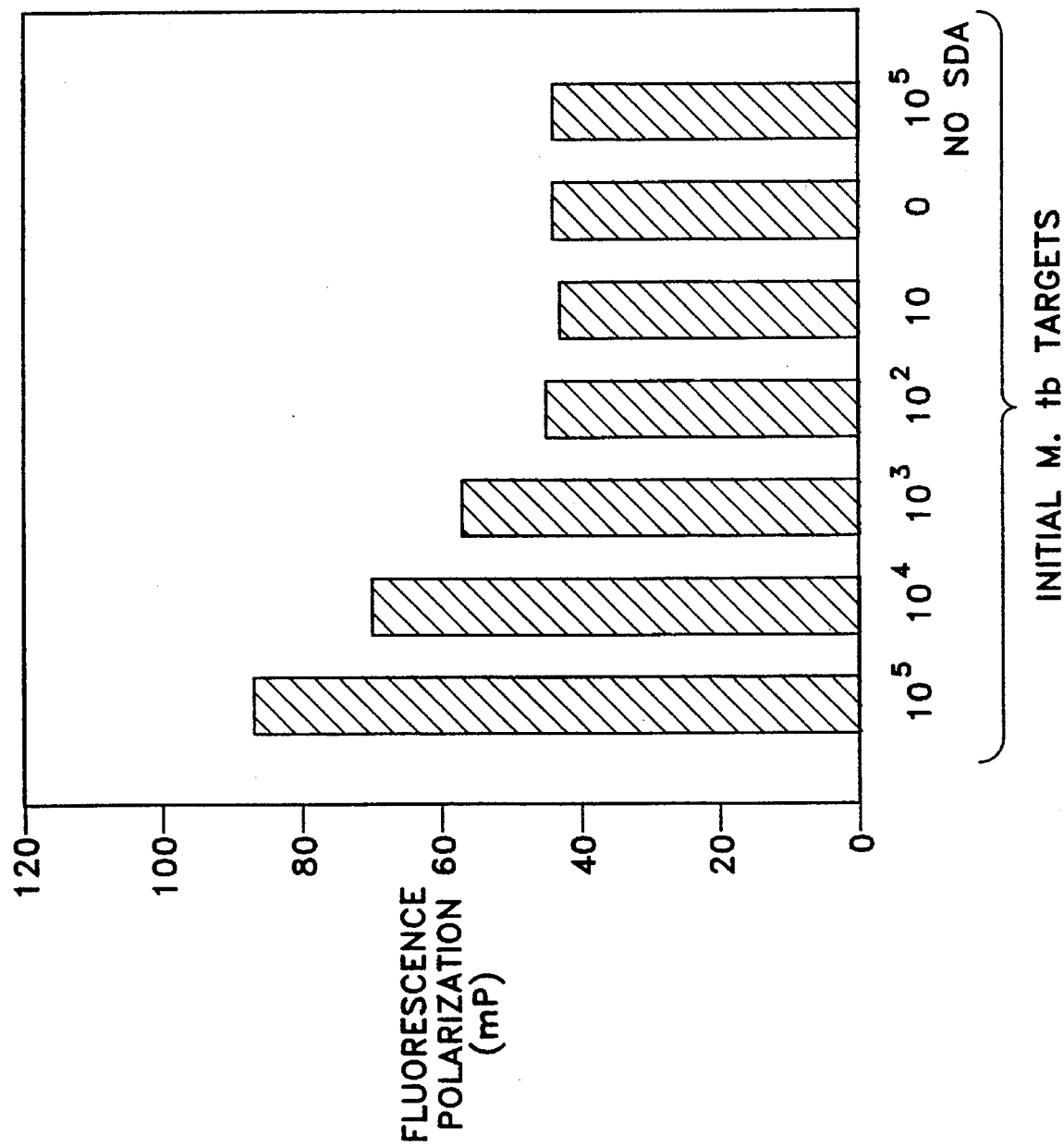
FIG. 9 is a graph showing the increase in FP associated with conversion of the detector probe to double-stranded form during amplification of an *M. tuberculosis* target sequence, with EcoRI (Gln 111) present during amplification.

Because SDA reactions contain magnesium, which activates EcoRI cleavage of doublestranded DNA, natural EcoRI cannot be present during SDA. It can be added post-SDA if enough EDTA is available to coordinate magnesium atoms. In contrast, EcoRI (Gln 111) does not cleave DNA even in the presence of magnesium. SDA was performed as in Example 6 in the presence of both SEQ ID NO: 6 and EcoRI (Gln 111). One µL of 8 µM EcoRI (Gln 111) was added to the SDA reaction at the time of addition of HincII and exo⁻ Klenow. Following SDA, the 100 µL samples were diluted with the appropriate buffers as in Example 4. After incubation at 37° C. for 20 minutes, these samples were read in the FPM 1 instrument over a 19 hour period, using disposable glass tubes. FIG. 9 shows the results after 1 hour of SDA.

In samples containing 1000 *M. tuberculosis* genomes or more, amplification was detectable above the controls which contained zero *M. tuberculosis* genomes. This sensitivity was less than that observed in Example 6, probably due to a general inhibition of SDA by EcoRI (Gln 111).

What is claimed is:

1. A method for detecting amplification of a double-stranded nucleic acid target sequence in a Strand Displacement Amplification reaction (SDA), the method comprising:

a) including in the SDA reaction a first amplification primer for SDA which hybridizes to a first strand of the target sequence, and a fluorescently-labeled single-stranded detector probe which hybridizes to the first strand of the target sequence downstream of the first amplification primer;

b) extending the first amplification primer and the detector probe on the target sequence, thereby producing (i) a detector probe extension product which is displaced from the first strand of the target sequence by extension of the first amplification primer and (ii) a first amplification primer extension product;

c) hybridizing a second amplification primer for SDA to the detector probe extension product and the first amplification primer extension product;

d) extending the second amplification primer on the detector probe extension product and the first amplification primer extension product, thereby converting the detector probe extension product to double-stranded form and amplifying the target sequence, and;

e) detecting an increase in fluorescence polarization as an indication of amplification of the target sequence.

2. The method of claim 1 wherein the detector probe is present in the SDA reaction at 50 pm–10 nM.

3. The method of claim 2 wherein the detector probe is labeled with La Jolla Blue™ or fluorescein.

4. The method of claim 2 wherein the the SDA reaction comprises about 0.25 units of polymerase and 100 nM of the first amplification primer.

5. The method of claim 1 wherein the increase in fluorescence polarization is detected during amplification by transient state fluorescence polarization.

6. The method of claim 1 wherein the increase in fluorescence polarization is detected after target amplification by steady state or transient state fluorescence polarization.

7. The method of claim 1 further comprising quantitating the initial concentration of the target sequence from the increase in fluorescence polarization.

8. The method of claim 1 wherein the target sequence is an *M. tuberculosis* target sequence.

9. A method for detecting amplification of a nucleic acid target sequence in an amplification reaction, the method comprising:

a) including in the amplification reaction a first amplification primer which hybridizes to a first strand of the target sequence and a fluorescently-labeled detector probe which hybridizes to the first strand of the target sequence downstream of the first amplification primer;

b) extending the first amplification primer and the detector probe on the target sequence, thereby producing (i) a detector probe extension product which is displaced from the first strand of the target sequence by extension of the first amplification primer and (ii) a first amplification primer extension product;

c) hybridizing a second amplification primer to the detector probe extension product and the first amplification primer extension product;

d) extending the second amplification primer on the detector probe extension product and the first amplification primer extension product, thereby converting the detector probe extension product to double-stranded form and amplifying the target sequence, and; e) detecting an increase in fluorescence polarization as an indication of target sequence amplification.

10. The method of claim 9 wherein the amplification reaction is SDA.

11. The method of claim 9 wherein the amplification reaction is PCR.

12. The method of claim 9 wherein the amplification reaction is 3SR.

13. The method of claim 1 wherein the SDA reaction further comprises a double-stranded DNA binding protein which binds to the double-stranded detector probe extension product.

14. The method of claim 9 wherein the amplification reaction further comprises a double-stranded DNA binding protein which binds to the double-stranded detector probe extension product.

15. The method of claim 14 wherein the detector probe comprises a recognition site for a double-stranded nucleic acid binding protein, and the amplification reaction further comprises the nucleic acid binding protein which binds to the recognition site.

16. The method of claim 9 wherein the amplification reaction further comprises an oligonucleotide which hybridizes to the double-stranded detector probe extension product.

17. The method of claim 13 wherein the detector probe comprises a recognition site for a double-stranded nucleic acid binding protein, and the SDA reaction further comprises the nucleic acid binding protein which binds to the recognition site.

18. The method of claim 17 wherein the detector probe comprises a recognition site for EcoRI and the SDA reaction further comprises EcoRI (Gln 111).

* * * * *